United States Patent
Sévigny et al.

(10) Patent No.: US 6,379,519 B1
(45) Date of Patent: Apr. 30, 2002

(54) DISPOSABLE THERMOFORMED ELECTROPHORESIS CASSETTE

(75) Inventors: Pierre Sévigny; Dominique Roy, both of Montréal (CA)

(73) Assignee: Mirador DNA Design Inc., Montreal (CA)

( * ) Notice: Subject to any disclaimer, the term of this patent is extended or adjusted under 35 U.S.C. 154(b) by 0 days.

(21) Appl. No.: 09/387,758

(22) Filed: Sep. 1, 1999

(51) Int. Cl.[7] .......................... G01N 27/26; B29C 31/06
(52) U.S. Cl. ...................................... 204/620; 264/267
(58) Field of Search ............................... 204/456, 466, 204/606, 616, 619, 620, 621; 264/267

(56) References Cited

U.S. PATENT DOCUMENTS

| | | | |
|---|---|---|---|
| 3,888,759 A | 6/1975 | Elson et al. | 204/620 |
| 4,294,684 A | 10/1981 | Serwer | 204/349 |
| 4,310,408 A * | 1/1982 | Rose et al. | 204/600 |
| 5,045,164 A | 9/1991 | Tansamrit et al. | 204/466 |
| 5,104,512 A * | 4/1992 | Gombocz et al. | 204/607 |
| 5,232,573 A | 8/1993 | Rosenvold | 204/620 |
| 5,512,157 A | 4/1996 | Guadagno et al. | 204/616 |
| 5,753,095 A | 5/1998 | Alpenfels et al. | 204/616 |
| 5,989,403 A * | 11/1999 | Provonchee | 204/619 |
| 6,214,191 B1 * | 4/2001 | Wiktorowicz et al. | 204/600 |

\* cited by examiner

*Primary Examiner*—Jill Warden
*Assistant Examiner*—Alex Noguerola
(74) *Attorney, Agent, or Firm*—France Côté; Swabey Ogilvy Renault

(57) ABSTRACT

The present invention is concerned with a disposable electrophoresis cassette particularly suitable for pre-cast polyacrylamide gels for protein and nucleic acid electrophoresis. The invention also comprises a support plate for the said cassette that acts as a heat sink and provides a more uniform migration front in operation since the temperature of the gel is substantially the same during electrophoresis operation. Also disclosed is a novel comb element for filling the cassette, and a novel method therefor.

18 Claims, 4 Drawing Sheets

DISPOSABLE THERMOFORMED ELECTROPHORESIS CASSETTE

FIELD OF THE INVENTION

The present invention is concerned with a disposable electrophoresis cassette particularly suitable for pre-cast electrophoretic media for protein and nucleic acid electrophoresis. The invention also comprises a support plate for the said cassette to ensure proper rigidity thereof into the electrophoresis apparatus, and acting as a heat sink, thus providing a more uniform migration front in operation because the temperature of the medium is substantially even anywhere inside the cassette during electrophoresis operation. The invention also comprises a comb for injection of electrophoresis medium into the cassette, as well as the corresponding method of injection.

BACKGROUND OF THE INVENTION

Electrophoresis is a well known separation technique that requires the application of electrical current at both poles of a cassette or plate to force samples through an electrophoretic medium that acts as a molecular sieve. The application of a difference of potential between the upper section and the lower section of the cassette assumes the creation of two areas sealed from each other. Because current is transmitted via two separate buffer reservoirs, it is necessary to apply a pressure or force on the cassette so that the seals properly operate. It is therefore imperative that the whole system, including the cassette, possess some rigidity.

Conventional electrophoresis cassettes are made of two glass plates spaced apart with plastic spacers or tongues to create a space therebetween while ensuring that the sides of the assembly are properly sealed. Importantly, the spacers must not conduct electrical current. The assembly is generally maintained together with clamps, and it is often necessary to reinforce the seals with hot agar. When the gel is cast into the cassette, a comb element is introduced at one end of the assembly to create one or more reservoirs or wells thereafter wherein the sample(s) will be received later. The shape of the comb may comprise various numbers and sizes of reservoirs, depending on the application required and the size of the cassette. For example, a preparation gel necessitate less reservoirs, while an analytical gel will require more reservoirs and the width thereof will depend on the resolution desired.

However, such assemblies have several drawbacks and limitations. The assembling operation requires dexterity and is a time-consuming operation, because it is done manually. The plates are conventionally made of glass, and thus must be handled with care. Further, they must be carefully cleaned to obtain good results. Finally, manipulation of acrylamide gel, a commonly used electrophoretic medium, represents a long-term danger for the health of operators since such gel is highly toxic.

More recently, to simplify the assembling work of operators and reduce poisoning and manipulation hazards, pre-cast cassettes already containing the gel have been made available commercially. The cassettes comprise an acrylamide gel, and a comb is provided at one extremity thereof However, the cost of these cassettes is prohibitive, and demolding thereof, for visualization of the results, is a delicate and complicated procedure. In addition, the comb is produced by injection molding, and is used to form the wells or reservoirs in the gel. They generally represent an important part of the total cost of the cassette.

To be economically feasible and capable of supporting, without substantial bending, the mechanical forces applied thereon, cassettes containing pre-cast electrophoresis medium, must be rigid enough and made of a material economically sound and preferably recyclable, such as for example thermoplastic materials like polymethylmethacrylate (PMMA). However, conventionally, in order to be sufficiently rigid, the plates must be relatively thick. Two obvious problems therefore become apparent: a) the amount of thermoplastic material required is significant, thus increasing the cost, which is not suitable for a disposable device; and b) maintaining the gel at an appropriate operating temperature is complicated, because the thick walls of the thermoplastic material act as a dielectric material. Thicker plastic walls also affect the diffusion of the heat generated during the electrophoretic process, creating temperature gradients within the electrophoresis medium, and non-uniform migration of the samples analyzed.

Conventional processes for filling the cassettes are generally standard, irrespective of the electrophoretic medium. Typically, a gel comprising a mixture of acrylamide and bis-acrylamide, a buffer like tris-borate ethylenediamine (EDTA), tris-acetate-EDTA, tris-glycine, tricine, and a polymerization initiator are injected or cast into the cassette. Some of these products are neurotoxic and/or irritant, and must therefore be handled with extreme care. A laboratory pipette or a pump can be used to fill the cassette from the top with the liquid medium. Once the cassette is filled, a comb closes the top of the cassette. The comb has a design such that it contains one or more teeth forming reservoirs in the gel wherein the sample will be placed later. After polymerization of the medium, the comb is removed, as well as a separator present in the lower portion of the cassette. The cassette is then placed in an electrophoresis apparatus wherein the lower and upper portions of the gel will be in contact with two independent buffer solutions. The samples are then introduced in the reservoirs, and current is applied to separate the various components of each sample. After completion of the separation, the medium is removed from the cassette for further processing, i.e., coloration, photograph and analysis.

Again, such system and procedure have various major drawbacks and limitations. As stated above, manual filling of the cassette requires great care and dexterity, not to mention exposure of the operator to toxic chemicals. Further, undesirable bubbles often form during filling, and installation of the comb after filling may also create bubbles at the bottom of the teeth. Such air bubbles must be avoided at all times, since they interfere significantly with the samples migrating in the polymerized gel during the electrophoresis procedure.

Pre-cast gels have been marketed recently, but have not been able to overcome other problems mentioned above for cassettes containing the same, such as prohibitive costs. One of the main reason is that the cassettes are obtained by injection molding, which is a costly and relatively slow process because of the significant amount of plastic required for injection, the cost of the plastic material itself, and the time necessary to allow complete cooling of the cassette thus obtained. In addition, because the cassettes are made of a thermoplastic material, gel polymerization is greatly affected and slowed down because the polymer absorbs free radicals generated by the chain reaction of the polymerization. As a result, the polymerized electrophoretic medium does not "stick" do the cassette inner surfaces. An expensive coating layer or overlay must therefore be applied on the thermoplastic material surfaces to minimize this problem and ensure proper polymerization quality and speed.

The electrophoresis operation necessitates the application of a voltage across the gel that generates heat that must be somehow dissipated. During the heat dissipation process, if the temperature of the gel is not uniform, it causes distortion in the separated protein or polynucleic acid bands. Such heat is therefore a critical problem because it limits the rate at which gels can be run. Increasing temperatures reduces the resistance and increases current at a given voltage. Although the net effect is a shorter run, excessive temperature can lead to undesirable band broadening. It is therefore preferable to run at a higher voltage and a constant lower temperature.

SUMMARY OF THE INVENTION

The present invention is concerned with an electrophoresis cassette comprising:

first and second thermoformed surfaces comprising their edges in hermetic contact with each other and defining a volume therebetween for receiving an electrophoretic medium;

either of first or second surface comprising at least one opened reservoir molded therein at one end; and either of first or second surface further comprising at least one aperture at an opposite end thereof.

In a preferred embodiment, the cassette comprises a male member having a structure complementary to that of the at least one reservoir, the male member being adapted to be removably inserted therein and further comprising:

an inlet and an outlet for injecting the electrophoretic medium therethrough and into the volume defined by the first and second surfaces; and at least one opening for discharge of the excess of the electrophoretic medium.

In a second aspect of the invention, there is provided a comb for an electrophoretic cassette adapted to be removably inserted into the cassette and allowing injection therein of an electrophoretic medium and discharge of excess of electrophoretic medium therefrom, comprising at least one inlet and one outlet for injection of the electrophoretic medium into the cassette, the outlet extending longitudinally on a first side of at least one tooth.

In a third aspect of the invention, there is provided an electrophoresis assembly comprising:

a cassette as defined above;

an electrophoretic medium comprised in the volume; and a support comprising a frame adapted to receive the cassette, the support further comprising a plurality of recesses forming corresponding channels between a cassette surface and the support, thus allowing passage of a coolant therein, whereby the temperature of the medium is substantially the same within the volume.

In a fourth aspect of the invention, there is provided a method for casting an electrophoretic medium into a cassette, comprising the steps of:

sealing any aperture present in the cassette;

injecting the electrophoretic medium into the inlet of the comb defined above, the medium penetrating into the volume through the comb; and continuing injection of the medium until all the volume is filled and an excess thereof is discharged from at least one opening of the comb.

Finally, in a fifth aspect of the invention, there is provided a composition for use as an electrophoretic medium comprising:

an electrophoretic gel;

a polymerization initiator;

a buffer; and an adhesive agent allowing adhesion of polymerized electrophoretic medium onto a surface of a thermoplastic electrophoretic cassette.

IN THE DRAWINGS

DETAILED DESCRIPTION OF THE INVENTION

The invention relates to the field of electrophoresis, and more particularly to a cassette suitable therefor. It is to be assumed that the gel used as the electrophoretic medium is preferably an acrylamide (or polyacrylamide) gel, whether cross-linked or not.

However, other conventional and well known electrophoretic media such as agarose gel or starch gel, can be used. Polyacrylamide gel is particularly preferred because it is transparent, electrically neutral, and can be made in various pore sizes. Other co-monomers well known in the field include N,N'-methylenebisacrylamide, N,N-bisacrylylcystamine, N,N'-(1,2-dihydroxyethylene) bisacrylamide, N,N'-diallyltartardiamide, and the like.

The drawings provided herewith are for the sole purpose of illustrating preferred embodiments of the invention, land shall not be considered as limiting the scope thereof.

Figure 1:
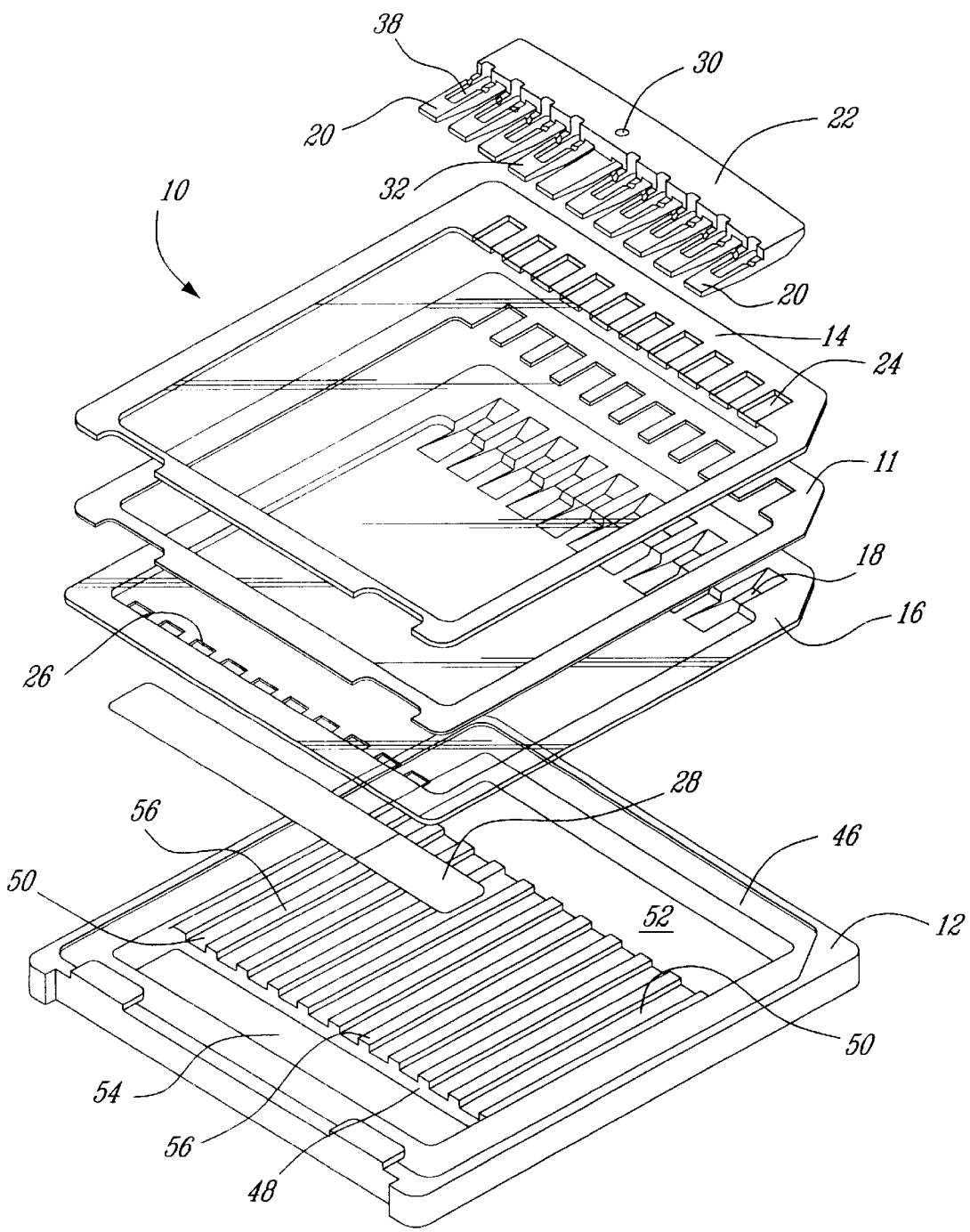
FIG. 1 illustrates a cassette and corresponding support plate in accordance with the present invention.
Figure 2A:
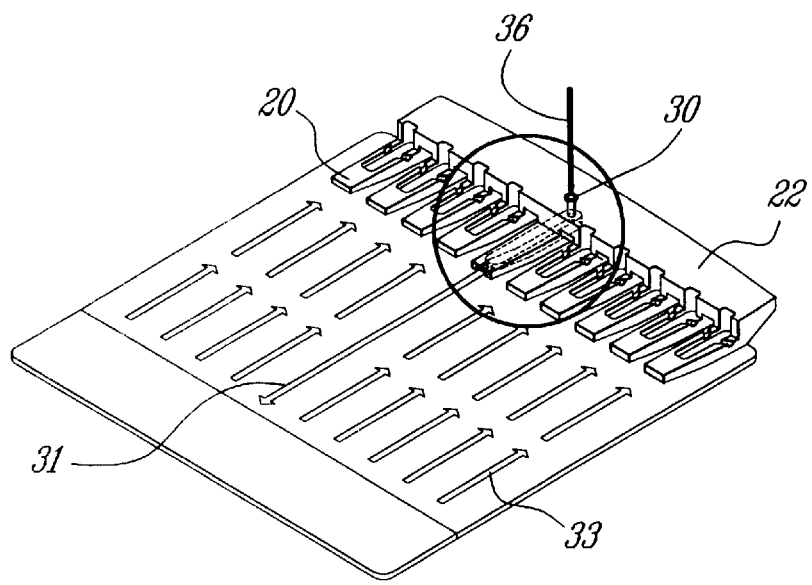
FIG. 2 illustrates the details of a comb developed in accordance with the present invention.
Figure 2B:
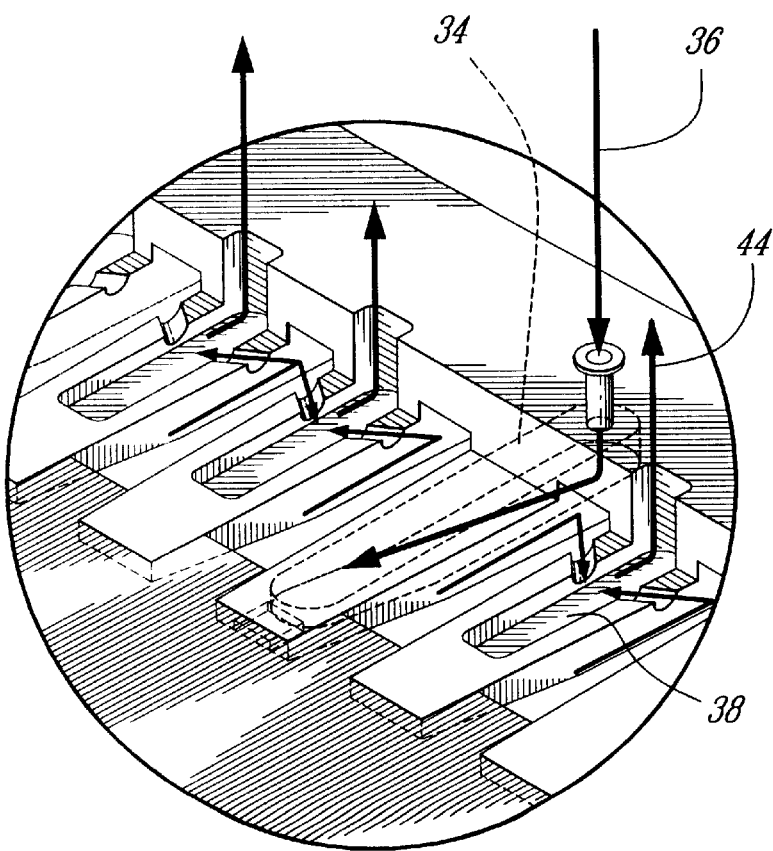
Figure 2C:
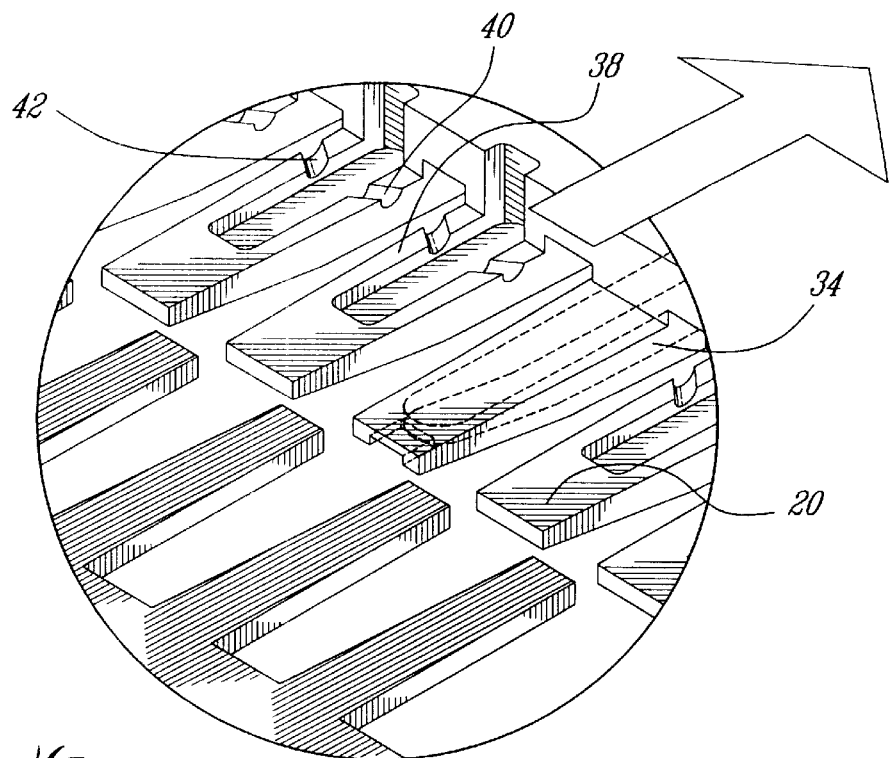
Figure 2D:
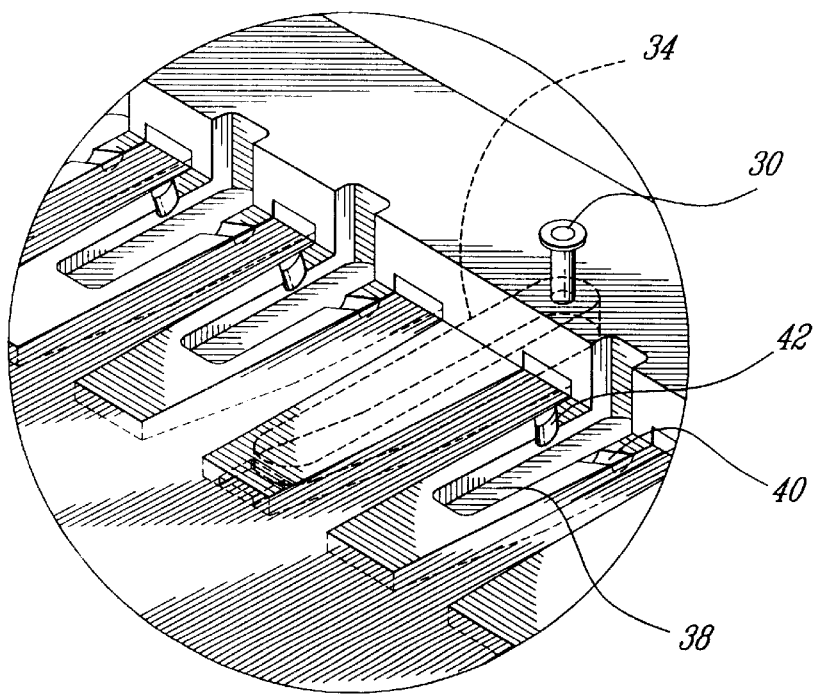
Figure 3:
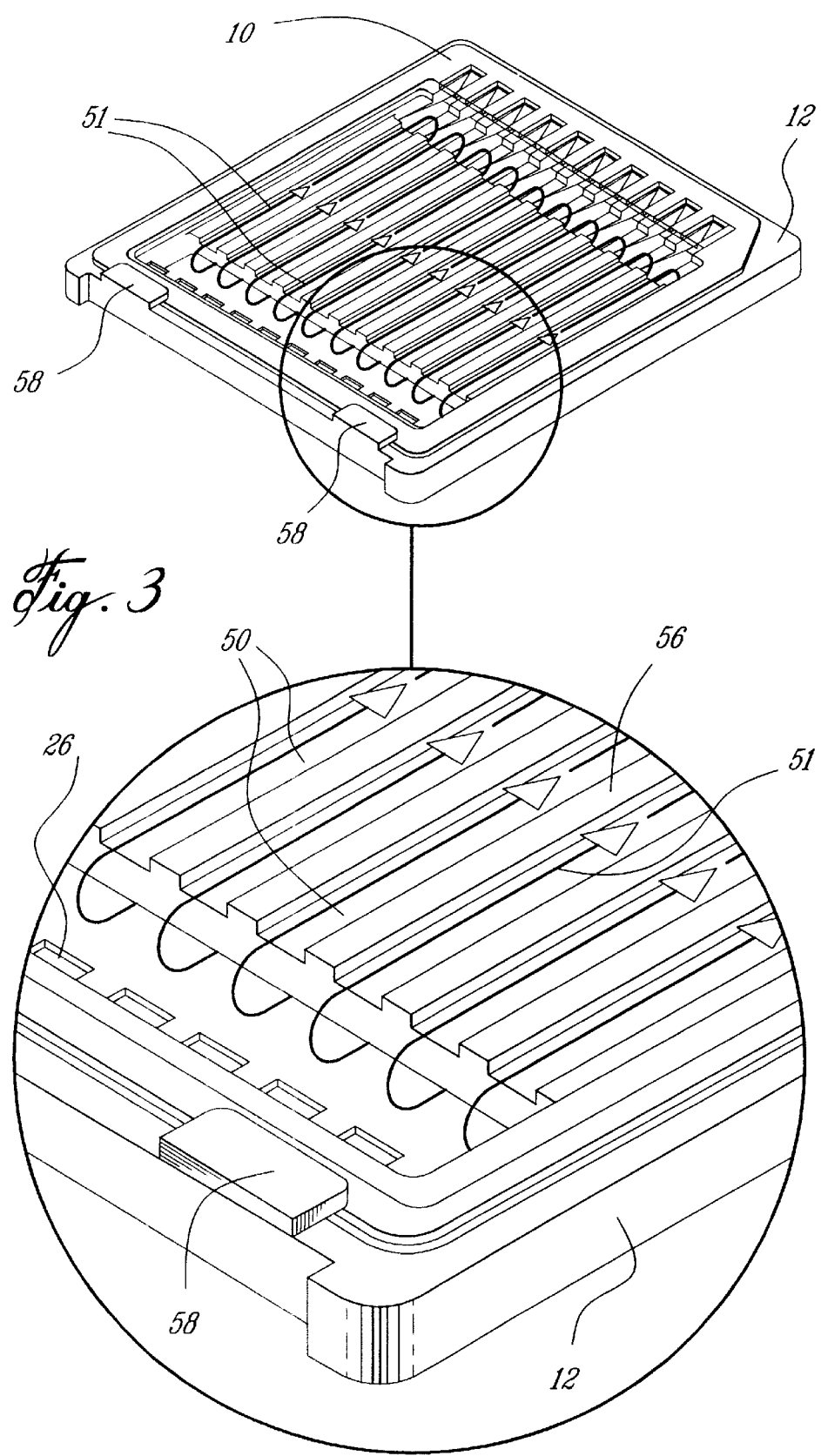
FIG. 3 illustrates the support plate developed for supporting the present cassette.

Referring to drawings, FIG. 1 illustrates a cassette assembly 10 and a support 12 therefor. Cassette 10 comprises a top plate 14 and a reservoir plate 16 each of a substantially square shape and having their four edges sealed, either with an adhesive layer 11 inserted therebetween, or with the help of any other compatible sealing means such as glue, ultrasonic welding, tape etc. The structure of layer 11 is complementary with that of both plates 14 and 16.

Plates 14 and 16 are preferably made of a chemically and electrically inert material having the desired degree of rigidity to support and protect the gel during casting thereof, as well as shipping and handling operations. A thermoplastic "thermoformable" material is most preferred because the plates can be produced commercially via sheet thermoforming, which is quick, reliable and relatively cheap. Preferred thermoplastic materials suitable for the purposes of the invention include any electrically and chemically inert thermoplastic material that can be easily and economically thermoformed. Most preferred examples are polystyrene, high density polyethylene (HDPE), low density polyethylene (LDPE), linear low density polyethylene (LLDPE), polyethylene terephtalate (PET), glycol-modified PET, polyethylene naphthalate, polyvinyl chloride (PVC), polyvinylidene chloride (PVDC), polycarbonate, PMMA, polyvinylacetate (PVA), ethylene vinylacetate (EVA), polypropylene, polyesters, cellulose acetates, polyamides such as nylon™, and copolymers thereof. Preferably, both plates 14 and 16 are made of the same material for compatibility purposes. In addition, at least reservoir plate 16 should be transparent, but it is preferred that both plates 14 and 16 be transparent.

Reservoir plate 16 comprises a series of reservoirs 18 for receiving a corresponding series of teeth 20 of comb 22. Top plate 14 has a complementary structure, i.e., a series of openings 24, that allow the passage therethrough of the plurality of teeth 20 for engagement into reservoirs 18. Reservoir plate 16 further comprises a series of slots 26 aligned with the series of reservoirs 18, and of substantially the same width. During filling, shipping and handling operations, these slots are sealed with a removable sealing strip 28 that will be removed before placing cassette 10 in the electrophoresis device. In an alternate embodiment, it has been found that the series of slots 26 can be replaced with slots having a smaller width but being present in a greater number, i.e, preferably twice the number of slots 26, with the same end result.

Comb 22 comprises an aperture or inlet 30 extending therethrough substantially perpendicularly to its longitudinal section, and aligned with a tooth 32, the latter comprising a longitudinal recess 34 shown in phantom lines in FIG. 2 and serving as an outlet. After engagement of teeth 20 into the series of reservoirs 18, an electrophoretic medium is injected into cassette 10 through aperture 30 and recess 34, as indicated by arrow 36. The flow of electrophoretic medium inside cassette 10 is also indicated by arrows 31 and 33. To ensure complete and proper filling of cassette 10, as well as minimizing air bubbles, a slight excess of electrophoretic medium must be injected. Such excess is discharged out of cassette 10 through a longitudinal recess 38 provided in each tooth 18. The flow of discharge is indicated by arrow 44. Recess 38 is located on the side of a tooth 20 that is opposite to the side of tooth 32 comprising recess 34. Each tooth 20 further comprises a pair of grooves 40 and 42, the depth of which being much smaller than that of recess 38, and arranged to form a V. The purpose of these grooves is mainly to facilitate gel separation from comb 22 upon removal thereof after completion of polymerization of the electrophoretic medium, although they may also be useful for discharge of excess of gel. Grooves 40 and 42 allow a clean separation of comb 22 from the gel, thus leaving a lower surface of reservoir 18 containing the medium substantially similar and even in each reservoir 18.

During the electrophoretic medium casting process, the medium is poured into cassette 10 through opening 30 of comb 22, and allowed to solidify. Preferably, the cassette is held in a manner such that plates 14 and 16 are kept substantially parallel to facilitate the filling of the cassette. Plates 14 and 16 can be kept substantially parallel by, for example, applying a tension on each side thereof to stretch its position, or a "non-sticky" glue is applied on the external surface of the plates, so that the latter can be removably "stuck" during injection of the electrophoretic medium therebetween. Alternately, a vacuum can be applied both outside and inside the cassette, i.e., inside for drawing the gel inside the cassette, and outside for maintaining the plates substantially parallel. A combination of vacuum outside and positive pressure inside the cassette may also be used. The polymerization process begins after an excess of medium has poured out of each recess 38, confirming complete filling of cassette 10. This method therefore substantially eliminates air bubbles from cassette 10. Once polymerization is complete, cassette 10 is stored appropriately in a conventional manner.

Comb 22 is preferably removed only minutes prior to the use of the cassette, or immediately after complete polymerization of the gel, prior to storage, if the reservoirs 18 are well preserved from dehydration. At that point, it is slowly pulled out of the cassette, and each reservoir 18 is thereafter filled with an appropriate volume of a sample to be electrophoresed.

It is well known that in operation, the temperature of the electrophoresis gel increases. It is also well known that the temperature will be higher towards the middle of the cassette than on the sides thereof. As a result, the migration front of the products to be separated is altered, and erroneous interpretation might occur. A novel support plate has therefore been developed to overcome these problems, as well as for providing a proper profile maintenance, i.e., sufficient rigidity of the thin walls of the cassette, and facilitating installation of the cassette into an operational position in a conventional electrophoresis apparatus.

Support plate 12 comprises a frame 46 adapted to receive therein cassette 10, and comprising a surface 48 with a plurality of longitudinal recesses 50, which can be of any shape and size. Openings 52 and 54 are cut within the plate to define a free space substantially corresponding in size to reservoir 18 and slots 26. When cassette 10 is placed onto support 12, it lies directly onto ridges 56 of plate 12, thus forming a series of channels between recesses 50 and a surface of cassette 10 for circulation of the buffer solution therein (flow indicated by arrows 51), and thus helping dispersing heat generated within the cassette. As illustrated, each recess 50 is preferably aligned with a reservoir 18 and a slot 26, to ensure that the temperature of the migrating product and the gel is substantially the same, whether the reservoir is near the side or the middle of the cassette. It has however been found that such alignment is not mandatory. The critical element is that some buffer solution is allowed to circulate between the support plate and the cassette to "extract" heat from the latter. Support 12 can be made of any suitably rigid material, but is preferably made of a heat conducting material, so that heat is also extracted from ridges 56 that are in direct contact with the surface of cassette 10 lying thereon, and dispersed within the structure of the support. Cassette 10 can be maintained in place in plate 12 with the help of a couple of retainer plates 58.

With respect to the problem of interference of the polymerization process caused by the thermoplastic material of the cassette, it has been found that by combining a powerful initiator generating more free radicals with an appropriate "sticking" agent in the gel composition, there is no longer a need to apply a costly protective layer over the thermoplastic surfaces. Examples of such initiators include ammonium persulfate and N,N,N,N-tetramethylethylenediamine (TEMED); 4-dimethylaminopropionitrile; 1-hydroxycyclohexyl phenyl ketone; 2,2-diethoxy-acetophenone; 2,2-dimethoxy-2-phenylacetophenone; 2',4'-dimethoxy-acetophenone; 2-hydroxy-2-methyl-1-propiophenone; 2-hydroxy-2-methyl-1-phenylpropan-1-one, and mixtures thereof. These strong initiators allow a substantially complete polymerization of the gel. However, the resulting polymerized gel does not stick to the plastic surface, which is critical, particularly in view of the fact that the cassette structure is relatively flexible. Detachment or unsticking of the polymerized electrophoretic medium from the cassette inner surfaces may lead to the introduction of undesirable air bubbles between the plastic surface and the gel, and may also cause irregularities in the medium structure, thus severely impairing the efficiency of the cassette. Surprisingly, it has been found that by adding to the gel composition a small amount of an adhesive compound is sufficient to allow the gel to adequately stick onto the plastic surface. The adhesive compound preferably corresponds to that used for coating the inner surfaces of currently available thermoplastic cassettes for the same purpose. However, the costs associated with the processing and coating of such a layer on the inner surfaces of the cassette are significant. On the other hand, in the present invention, all one has to do is to add a sufficient amount of the said adhesive compound into the gel composition to be injected into the cassette to achieve the same result. Not only is the procedure more simple, but the amount of adhesive compound required is smaller. Suitable adhesive compounds include polysilazanes or tetra-substituted silicon derivatives. The substituents can be the same or different, and include a straight or branched alkyl, alkoxy, ketone, ester or amide each comprising from 1 to 8 carbon atoms, or an amino, halogen, cyano or hydroxy. Preferred adhesives are alkyl alkoxy silane derivatives. Most preferred adhesives include Silane A-174, methacryloxytrimethoxysilylpropane, 3-(trimethoxysilyl) propyl methacrylate, 3-methacryloxypropyltrimethoxysilane, MEMO, DYNASYLAN MEMO, and γ-methacryloxypropyltrimethoxysilane.

The thickness of plates 14 and 16 should be sufficient to be rigid enough for operation in an electrophoresis system. For economical purposes, it has been found that it is not necessary to exceed a thickness of about 40/1000.

While the invention has been described in connection with specific embodiments thereof, it will be understood that it is capable of further modifications, and this application is intended to cover any variations, uses or adaptations of the invention following, in general, the principles of the invention, and including such departures from the present description as come within known or customary practice within the art to which the invention pertains, and as may be applied to the essential features hereinbefore set forth, and as follows in the scope of the appended claims.

What is claimed is:

1. An electrophoresis cassette comprising:
   first and second surfaces comprising their edges in hermetic contact with each other and defining a volume therebetween for receiving an electrophoretic medium;
   either of first or second surface comprising at least one opened reservoir molded therein at one end; and
   either of first or second surface further comprising at least one aperture at an opposite end thereof;
   wherein the first surface comprises a reservoir plate comprising the at least one reservoir in an upper portion and apertures in a lower portion, and wherein the second surface comprises a top plate comprising at least one opening aligned with the at least one opened reservoir of the reservoir plate.

2. A cassette according to claim 1 further comprising a male member having a structure complementary to that of the at least one reservoir, the male member being adapted to be removably inserted therein and further comprising:
   an inlet and an outlet for injecting the electrophoretic medium therethrough and into the volume defined by the first and second surfaces; and
   at least one opening In said male member for discharge of the excess of the electrophoretic medium.

3. A cassette according to claim 2 wherein the male member comprises a comb comprising a number of teeth corresponding to the number of reservoirs, each tooth having a structured to adapted cooperatively and removably image into the at least one opened reservoir.

4. A cassette according to claim 3, wherein the outlet extends longitudinally on a first side of a tooth.

5. A cassette according to claim 4, wherein at least one tooth comprises a recess extending longitudinally on a second side opposite to the first side, for discharge of excess of electrophoretic medium.

6. A cassette according to claim 5, wherein the recess comprises a groove on each side thereof, to form a v-shaped groove.

7. A cassette according to claim 1, wherein an adhesive layer is inserted between the first and second surfaces.

8. A cassette according to claim 1, wherein both first and second surfaces are made of a substantially transparent, non-conductive material and chemically inert material.

9. A cassette according to claim 8, wherein the material comprises polystyrene, high density polyethylene (HDPE), low density polyethylene (LDPE), linear low density polyethylene (LLDPE), polyethylene terephtalate (PET), glycol-modified PET, polyethylene naphthalate, polyvinyl chloride (PVC), polyvinylidene chloride (PVDC), polycarbonate, PMMA, polyvinylacetate (PVA), ethylene vinylacetate (EVA), polypropylene, polyesters, cellulose acetates, polyamides, and copolymers thereof.

10. An electrophoresis assembly comprising:
    a cassette according to claim 1;
    an electrophoretic medium comprised in the volume; and
    a support comprising a frame adapted to receive the cassette, the support further comprising a plurality of recesses forming corresponding channels between a cassette surface and the support, thus allowing passage of a coolant therein, whereby the temperature of the medium is substantially the same within the volume.

11. A method for casting an electrophoretic medium into a cassette according to claim 2 comprising the steps of:
    sealing the at least one aperture;
    injecting the electrophoretic medium into the inlet, the medium penetrating into the volume through the male member; and
    continuing Injection of the medium until all the volume is filled and an excess thereof is discharged from the at least one opening of the male member;
    wherein said injection provides said casting of said electrophoretic medium.

12. A method according to claim 11 wherein the electrophoretic medium is polymerized immediately after casting, or just prior to use of the cassette.

13. A method according to claim 11 wherein the male member comprises a comb comprising a number of teeth corresponding to the number of reservoirs, each tooth having a structure adapted to cooperatively and removably engage into the at least one reservoir.

14. A method according to claim 13 wherein the outlet extends longitudinally on a first side of a tooth.

15. A method according to claim 14, wherein at least one tooth comprises a recess for discharge of the electrophoretic medium, the recess being a second side opposite to the first side of the tooth.

16. A method according to claim 15, wherein the recess comprises a groove on each side thereof, to form a v-shaped groove.

17. An electrophoresis cassette comprising:
    first and second surfaces comprising their edges in hermetic contact with each other and defining a volume therebetween for receiving an electrophoretic medium;
    either of first or second surface further comprising at least one opened reservoir formed therein at one end; and
    either of first or second surface further comprising at least one aperture at an opposite end thereof;
    male member having a structure complementary to that of the at least one reservoir, the male member being adapted to be removably inserted therein and further comprising:
    an inlet and an outlet for injecting the electrophoretic medium therethrough and into the volume defined by the first and second surfaces; and at least one opening In said male member for discharge of the excess of the electrophoretic medium;

wherein the male member comprises a comb comprising a member of teeth corresponding to the member of reservoir each tooth having a structure adapted to cooperatively and removable engage into the at least one opened reservoir.

18. A method for casting an electrophoretic medium into a cassette comprising:

first and second surfaces comprising their edges in hermetic contact with each other and defining a volume therebetween for receiving an electrophoretic medium;

either of first or second surface comprising at least one opened reservoir formed therein at one end; and either of first or second surface further comprising at least one aperture at an opposite end thereof;

a male member having a structure complementary to that of the at least one reservoir, the male member being adapted to be removably inserted therein and further comprising:

an inlet and an outlet for injecting the electrophoretic medium therethrough and into the volume defined by the first and second surfaces; and at least one opening for discharge of the excess of the electrophoretic medium;

said method comprising the steps of:

sealing the at least one aperture;

injecting the electrophoretic medium into the Inlet, the medium penetrating into the volume through the male member; and continuing injection of the medium until all the volume is filled and an excess thereof is discharged from the at least one opening of the male member;

wherein said injection provides said casting of said electrophoretic medium.

* * * * *